United States Patent [19]

Meek

[11] 3,949,075

[45] Apr. 6, 1976

[54] ANTI-MICROBIAL COMPOUNDS OF 2', 4' SUBSTITUTED ANILIDES OF SUBSTITUTED NITROSALICYLIC ACID FOR QUADRUPED ANIMALS

[75] Inventor: William H. Meek, Northfield, Ohio

[73] Assignee: Ferro Corporation, Cleveland, Ohio

[22] Filed: May 1, 1974

[21] Appl. No.: 465,884

Related U.S. Application Data

[63] Continuation-in-part of Ser. No. 277,076, Aug. 1, 1972, Pat. No. 3,839,443, which is a continuation-in-part of Ser. No. 186,514, Oct. 4, 1971, abandoned.

[52] U.S. Cl. .............................................. 424/230
[51] Int. Cl.² ........................................ A61K 31/60
[58] Field of Search ................................... 424/230

[56] References Cited
UNITED STATES PATENTS 3,449,420  6/1969  Ruschig et al. ..................... 424/230
3,646,199  2/1972  Schellenbaum et al. ............. 424/230

*Primary Examiner*—Sam Rosen
*Attorney, Agent, or Firm*—Milton L. Simmons; Wesley B. Taylor

[57] ABSTRACT

A class of organic compounds is disclosed comprising substituted anilides of 3-tert. butyl-6-methyl-5-nitrosalicylic acid, characterized in that the anilide portion is substituted only in the 4' position or only in the 2', 4' positions from a relatively small number of monovalent substituents. Such compounds are useful in the control of microorganisms and especially as anthelmintics, that is, therapeutic agents for destroying parasitic life, such as intestinal worms. Certain of the compounds are especially effective against Nematodes such as Haemonchus and Trematodes such as Fasciola.

14 Claims, No Drawings

ANTI-MICROBIAL COMPOUNDS OF 2', 4' SUBSTITUTED ANILIDES OF SUBSTITUTED NITROSALICYLIC ACID FOR QUADRUPED ANIMALS

CROSS-REFERENCE TO RELATED APPLICATIONS

This application is a continuation-in-part of an application filed Aug. 1, 1972, Ser. No. 277,076, now U.S. Pat. No. 3,839,443, which is a continuation-in-part of an application filed Oct. 4, 1971, Ser. No. 186,514, now abandoned. Other related U.S. patents include U.S. Pat. Nos. 3,801,637 and 3,888,890.

BACKGROUND OF THE INVENTION

The need for combating the growth of undesirable microorganisms, bacteria, insects, and the like is a continuing and increasing one. Many organic compounds have been suggested as a deterrent to such growth or as an effective destroyer of the undesired life.

As compared to a mere killing or destroying of microorganisms, etc., a quite different situation prevails when one is concerned with killing only one of two cohabiting classes of living things without harming the other. A common example of this is undesirable parasitic infestation on a desirable, living, warm-blooded, animal.

More specifically, various types of worm parasites are found in mammals of commercial importance to man. The most important are the parasites of livestock, especially of ruminants, such as sheep, goats, and cattle. However, other ruminants are similarly affected such as oxen, deer, water buffalo, etc. The more significant parasites are the nematodes (worms) of the alimentary tracts and the trematodes (flukes) which infect the liver. The alimentary tract nematodes are principally important insofar as they raduce the growth of the host animals and render less efficient the consumption of feed by the animals. The trematodes directly affect a vital organ and can cause severe illness and death in the host animal.

Obviously, a treating agent which not only kills parasites, but also kills the host animal is of no utility. Conversely, a treating agent that is harmless on the host animal but only slightly retards the growth of parasitic life is of little real value. What is needed is a treating agent that not only kills or expels the parasites, but which is harmless to the host; or for which the host has a large margin of tolerance, that is, an agent of which the host can take massive dosages with little or no harm. Moreover, although both types of mentioned infestations, the nematodes and the trematodes, occur commonly and naturally in the same types of livestock, presently known medications normally used for control on one of these infections is generally ineffective for the control of the other.

The matter of tolerance of a host animal for a therapeutic agent, such as an anthelmintic, cannot be overemphasized, especially when the animal must be administered to from a group or herd of animals in an unavoidably somewhat imprecise manner. In the treatment of large groups there is serious risk that some animals may be inadvertantly treated more than once, and thus subjected to double or triple dosage; that some animals will be overdosed because of errors in estimating their individual weights; that some animals will, by virtue of individual genetic variation, and variable state of health or ability, have less tolerance than the average animal for any medication, It is therefore clearly desirable that the typical animal be able to tolerate without serious harm, as large a multiple as possible of the minimum dosage regarded a likely to be effective as an anthelmintic.

The difference in activity between an effective amount of an anthelmintic on parasites and on a host animal can be quantitatively expressed as a Therapeutic Index. This index is defined as the maximum dose at which no toxic symptoms in the host animal are observed, divided by the minimum dose at which the anthelmintic is therapeutically effective. In general, an anthelmintic is considered to be therapeutically effective against a given parasite when it kills or expels from the host at least 80% and preferably close to 100% of the viable forms of that parasite.

SUMMARY OF THE INVENTION

It has now been discovered that a class of compounds comprising substituted anilides of 3-tert.-butyl-6-methyl-5-nitrosalicylic acid have particular utility as a control for various types of microorganisms and also make effective anthelmintics against both nematodes and trematodes when substituted only in the 4' position on the anilide moiety, or when substituted only in the 2' and 4' positions, and no other positions. Additionally, the substituents themselves must be selected from a rather limited class. Still further, when these substituents are reduced to an even more limited class, the resulting compounds make superior anthelmintics. The latter compounds are not only highly efficient in killing a wide spectrum of parasites but can be tolerated without harm by host animals in relatively large amounts.

A compound of the present invention has the general formula:

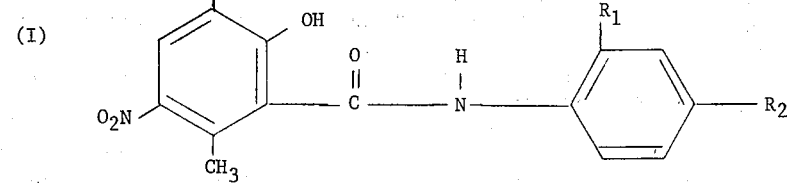

(I)

in which $R_1$ is H, chloro, bromo, iodo, $CF_3$, or alkyl of 1 to 4 carbon atoms, such as methyl or ethyl, and $R_2$ is chloro, bromo, iodo or $CF_3$.

The compounds of Formula I in which $R_1$ is methyl or $CF_3$, and $R_2$ is chloro, bromo, iodo or $CF_3$ are preferred. The compounds in which $R_1$ is $CF_3$ and $R_2$ is chloro or bromo are most advantageous.

DESCRIPTION OF THE PREFERRED EMBODIMENTS

Here and in the claims the following number system of salicylanilides is used:

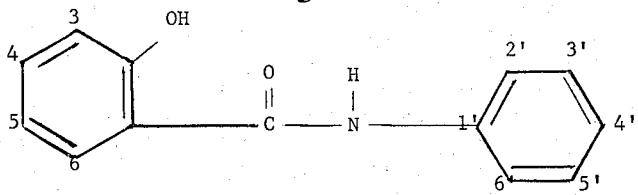

The salicylic acid portion of all compounds of the present invention have the same molecular configuration to afford the most useful compounds, namely, hydroxyl at the 2 position as indicated, tert. butyl at the 3 position, nitro at the 5 position, and methyl at the 6 position. The anilide portion of all compounds of the present invention are substituted in only one or only two specific positions and at no other positions, namely, at the 4' position only or at the 2' and 4' positions only.

Additionally, the substituents at the 2',4' positions must be selected from a relatively small group of monovalent substituents. As indicated, referring to the Formula I of the preceding section, $R_1$ must be H, chloro, bromo, iodo, $CF_3$, or alkyl of 1 to 4 carbon atoms, and $R_2$ must be chloro, bromo, iodo or $CF_3$. Anthelmintics of superior properties and performance are obtained when $R_1$ is restricted to $CF_3$ and $R_2$ is restricted to chloro or bromo.

Preparation of compounds of the present invention are described in the cited parent application, Ser. No. 186,514. In general, 3-tert. butyl-6-methylsalicylic acid may be nitrated in toluene solution with dropwise addition of nitric acid for about an hour at about 65°C. to about 70°C. Upon cooling, 3-tert. butyl-6-methyl-5-nitrosalicylic acid precipitates and may be recovered by filtration.

The anilide of the described salicylic acid may then be formed by reacting the acid with a phenylamine, the phenyl nucleus having the desired substituent or substituents. This reaction may be carried out in toluene solution at 110°C. under reflux conditions for four to six hours in the presence of a condensing agent such as $POCl_3$ or $PCl_3$. Upon cooling, a precipitate of a substituted anilide of 3-tert.butyl-6-methyl-5-nitrosalicylic acid forms which can be recovered by filtration, washing, and drying.

The new method of controlling helminths or parasitic worms by this invention comprises administration to a host animal such as a ruminant animal in need of such treatment orally alone, combined with a pharmaceutical or a feed carrier, an effective anthelmintic but nontoxic quantity of a compound of Formula I. In certain cases such as extragastrointestinal infestation of flukes as in sheep, the compounds may be administered parenterally, that is, in a sterile micronized suspension or solution.

The administration is in quantities nontoxic but effective either for curative or prophylactic purposes and has broad range of activity on gastrointestinal parasites of warm-blooded animals especially sheep and cattle. The helminths most effectively treated with the new compounds are the Trematodes, Cestodes or, and especially, Nematodes. Activity against flukes such as *Fasciola gigantica* or *Fasciola hepatica* is also particularly pronounced as noted above. More specific parasitic infestations in which this invention may be applied are found in the Merck Veterinary Manual, Third Edition, pages 699-806, as are general methods of control of internal parasites; see also U.K. 1,183,641. Generally effective but nontoxic dose ranges of the active ingredients are selected from about 0.25 mg./kg. of body weight up to about 50 mg./kg. and preferably about 0.5 to 10 mg./kg. Effective dosages in sheep without significant side effects have been found to be about 0.25 to 50 mg./kg., with the monosubstituted compounds at $R_2$ ($R_1$ being hydrogen) being less toxic and less active within this range. The disubstituted compounds are the preferred compounds and, as compared with the monosubstituted compounds, are much more active and somewhat more poorly tolerated, although with a better therapeutic ratio. Most usually the dosage unit compositions are administered from 1 to 5 times daily, preferably for convenience one treatment is used to clear the infection. The dose range for the preferred compounds, in which $R_1$ is trifluoromethyl and $R_2$ is chloro or homo, is from about 0.25 to 25 mg./kg. of body weight and preferably about 0.5 to 10 mg./kg. The advantageous bromo congener is used most generally at about 3 mg./1 kg., usually as a drench, paste, bolus or top dressing.

Veterinary or compositions containing sufficient quantities of the compounds of Formula I to reach the dose levels mentioned above are prepared as known to the art by preparing tablets, capsules, boluses, liquid suspensions, powders, drenches or solutions for injection in packaged form. Alternatively, especially for prophylaxis, premix or feed compositions containing effective but nontoxic quantities of the active salicylanilide are used. For these purposes particulate carriers, inert powders or, especially, feed carriers such as soybean meal, corn oil, vermiculite, diatomaceous earth, barley or wheat are used. In dosage unit or premix feed compositions the compound can comprise from about 5% to 75% by weight of the final composition as is convenient for the farmer or veterinarian. As an example, a 5% salicylanilidevermiculite or soybean meal premix can be used which will be uniformly mixed with the animal foodstuff. Alternatively, a lick or pasture block can be used for field animals.

To show the relative effect of compounds of the present invention differing in the $R_1$ and $R_2$ substituents of Formula 1, as well as to show the relative effect of those compounds with respect to still other related compounds which are not of the present invention, that is, in which $R_1$ and $R_2$ are monovalent substituents other than those claimed, a series of tests were carried out on living animals as follows.

Two groups of sheep were used in the tests. One group was used as a non-medicated control, while the other group was treated with the compound under investigation. Helminth-free young lambs were infected with about 10,000 filariform larvae of *Haemonchus contortus*. In three weeks when the infection became apparent, egg counts were made to determine the density of the worm burden.

The egg count was carried out using the following modified Stoll method. Three grams of sheep feces were taken rectally from each animal and placed in a Stoll flask. To each flask, tap water was added to the top line. The fecal pellets were too hard to break down, the flasks were closed with rubber stoppers and kept in the refrigerator for several hours. The flasks were thoroughly shaken and a 1 ml. sample was drawn from the middle using a wide mouth pipette. This 1 ml. sample was transferred to an 8 ml. plastic tube, to which enough saturated sodium chloride solution was added to reach the rim. The tubes were then centrifuged for 10 minutes at 1500 r.p.m. Then sodium chloride solution was added with a medicine dropper forming a concave miniscus. A cover glass was carefully added and the tubes were kept in a refrigerator for ten to twenty minutes. During that period, the nematode ova flowed upward and adhered to the bottom of the cover glass slip. At the end of the 20-minute period, the cover slip was carefully detached from the miniscus and transferred to a microscopic slide. The ova were then counted under a microscope equipped with 10X ocular and 10X objective lens. Each ovum under the microscope represented 20 ova in the sample.

Animals with sufficiently high egg counts were taken out of the pool and housed in experimental pens. Since the salicylanilides of the present invention are water insoluble, the compounds were first ground using a mortar and pestle and then were placed in a carboxymethyl cellulose solution. The particles were further micronized ultrasonically. The compound was then administered to two or three animals by Oesophageal gavage. Control, untreated animals, received only the carboxymethyl cellulose solution in a similar manner. On the sixth and seventh day after treatment, fecal pellets were taken from the rectum of the control as well as the treated animals and egg counts were made.

Test for activity against liver flukes were conducted as follows:

Eggs of *Fasciola hepatica* were collected from the bile of donor sheep. The eggs were embryonated and snails were infected (the genus Lymnaea serves as intermediate host) to produce Metacercariae which are the infective forms for sheep. Each sheep was infected with 250 metacercariae intraruminally. When the infection became patent in ca. 80 days, egg counts were carried out to determine the degree of worm burden. The liver was processed to recover *F. hepatica* in the untreated and treated sheep.

The following examples illustrate the present invention and should not be construed as imposing limitations upon the claims. Percentages are by weight percent unless otherwise indicated.

Although the present compounds are uniquely adapted for use as anthelmintics, they also find use in the control of various types of microorganisms.

EXAMPLE 1

The following procedure for antibacterial evaluation was used. Test compounds were dissolved in a suitable solvent (typically dimethyl sulfoxide or acetone) and incorporated in a nutrient agar at various concentrations. The plates were then streaked with cultures of the appropriate bacteria. The inoculum contained about $8 \times 10^8$ organisms per milliliter. After incubation for 48 hours at 37°C., the plates were examined for evidence of growth of the microorganisms. The minimum concentration necessary for complete inhibition of growth was noted.

For testing against the fungus Trichophyton the same procedure was used, except that the test medium was Sabouraud agar, and the plates were cultured for 120 hours at 25°C. before evaluation for evidence of growth. The inoculum added to the culture media contained about $5 \times 10^6$ spores in a water suspension containing 0.1% peptone.

Thus 4'-bromo-3-tert. butyl-6-methyl-5-nitrosalicylanilide was observed to have the following minimum inhibitory concentrations in agar plate tests against bacteria.

| Minimum Inhibitory Concentration (ppm) | |
|---|---|
| Staphylococcus aureaus | 1 |
| Haemophilus gallinarum | 8 |
| Escherichia coli | 64 |
| Streptococcus foecalis | 64 |
| Salmonella choleresuis | 64 |
| Salmonella gallinarum | 64 |

The same compound was also found to be effective in reducing infestation on tomatoes by the fungi responsible for early blight (*Alternaria solani*) and late blight (*Phytophthora infestans*).

The compound, 3-tert. butyl-4'-chloro-6-methyl-5-nitrosalicylanilide, is inhibitory at 1 ppm to *Trichophyton mentagrophytes*, a fungus causing certain mamalian skin disorders.

Example 2

| Sheep Drench | Parts by Weight |
|---|---|
| 3-tert.Butyl-2', 4'-dichloro-6-methyl 5-nitrosalicylanilide | 20 |
| Terra alba | 75.5 |
| Tragacanth | 3.0 |
| Sodium lauryl sulfate | 1.5 |
| Water | |

The above solid components are mixed to give a water-dispersible powder to be used on concentrations of 5 grams of powder to 5 ml. of water. The drench is used orally as necessary and practical to control gastrointestinal infections.

Example 3

| Ruminant Bolus | Grams |
|---|---|
| 3-tert.Butyl-4'-chloro-2', 6-dimethyl 5-nitrosalicylanilide | 0.5 |
| Calcium phosphate | 4.0 |
| Maize starch | 0.54 |
| Talcum | 0.14 |
| Gum arabic | 0.15 |
| Magnesium stearate | 0.05 |

The phosphate and salicylanilide are mixed and screened, then granulated using one-half the starch. The screened and dried granules are mixed with the remaining ingredients, blended thoroughly and compressed on a bolus press.

Similarly, tablets can be prepared with reduced fillers.

EXAMPLE 4

The compounds of this invention also have utility against liver flukes. When administered an oral dosage of 5 milligrams per kilogram of body weight of sheep infected with liver flukes of the genus Fasciola, 3-tert. butyl-2', 4'-dichloro-6-methyl-5-nitrosalicylanilide, completely destroyed all flukes within three days. Against immature fluke infestations in sheep similar activity was found at 15 mg./kg. The same effects against mature flukes were observed when 3-tert. butyl-4'-chloro-2', 6-dimethyl-5-nitrosalicylanilide was administered at 5 milligrams per kilogram of body weight. The 4' bromo congener was active against mature flukes at 15 mg./kg. By contrast the isomeric compound 3-tert. butyl-3'-chloro 2', 6-dimethyl-5-nitrosalicylanilide is ineffective against liver flukes even when the sheep receive 15 milligrams per kilogram of body weight.

Other compounds of this invention which were tested and found efficacious at 15 milligrams per kilogram of sheep body weight were: 3-tert. butyl-6-methyl-5-nitro-4'-trifluoromethylsalicylanilide and 3-tert. butyl-4'-chloro-6-methyl-5-nitrosalicylanililde.

In this respect, compounds of this invention differ from compounds currently in commercial use which are not effective against both gastrointestinal worms and liver flukes. Since the simultaneous occurrence of both forms of infections is common in commercial ruminant husbandry, the value of a single form of medication to cure both types of infection if self-evident.

EXAMPLES 5 THROUGH 13

The results of tests on sheep in a manner described, supra, using compounds of the present invention are given in Table 1, Examples 5 through 13. The numbers in the column headed "Haemonchus (15 mg/kg)" refer to the percent of parasites destroyed or expelled when the indicated compound was introduced into the rumen of sheep at a dosage of 15 milligrams per kilogram of body weight. The values under "Tolerance (mg/kg)" refer to the highest test dosage in the milligrams of anthelmintic per kilogram of body weight at which the sheep developed no toxic symptoms. "Tol." is an abbreviation for "tolerated". The symbols $R_1$ and $R_2$ refer to those of Formula I in these and other following examples.

1971, first compound on page 5) has only 61% activity at 5 mg./kg. and shows toxic effects at 50 mg./kg. It will be appreciated that only a 60% reduction in worm burden is not a practical or commercial objective for a new anthelmintic. The Monsanto patent also disclosed the salicylanilides only as larvicidal compounds against Lepidoptera or chewing insects. It discloses no activity against internal parasites such as pin worms, round worms, flukes, etc. where a principal use of this invention lies.

EXAMPLES 14 THROUGH 22

When compounds of Formula I were used on sheep having substituents in the 2' and 4' positions, other than those herein disclosed and claimed, the results were quite poor. Table II summarized the data for such other substituents.

Table II

| Example | $R_1$ | $R_2$ | Effectiveness in removal of Haemonchus at an intrarumenal dosage of 15 mg/kg |
|---|---|---|---|
| 14 | $CF_3$ | H | 0 |
| 15 | F | H | 0 |
| 16 | Cl | H | 33 |
| 17 | Br | H | 0 |
| 18 | I | H | 0 |
| 19 | H | $SO_2NH_2$ | 0 |
| 20 | H | $CO_2C_2H_5$ | 18 |
| 21 | $CH_3$ | $CH_3$ | 13 |
| 22 | $OCH_3$ | Cl | 10 |

EXAMPLES 23 THROUGH 26

The importance of the 2',4' substitution on the anilide moiety of Formula I is illustrated by the case of the Table 1

| Example | Substituents $R_1$ | $R_2$ | Haemonchus (2 mg/kg) | Haemonchus (5 mg/kg) | Haemonchus (15 mg/kg) | Tolerance (mg/kg) |
|---|---|---|---|---|---|---|
| 5 | Cl | Cl | 14 | 100,99 | 100 | >50,<100 |
| 6 | $CH_3$ | Cl | 67 | 95,99 | 100 | >50,<100 |
| 7 | H | Cl | 0 | 65 | 81 | >15,<50 |
| 8 | H | Br | — | — | 61 | — |
| 9 | H | I | 14 | 22 | 93 | — |
| 10 | H | $CF_3$ | — | — | 100 | >15,<50 |
| 11 | $CF_3$ | Br | 99.8 | — | — | Tol. at 20 |
| 12 | $CF_3$ | Br | — | 100 | — | Tol. at 35 |
| 13 | $CF_3$ | Cl | 96 | 91 | 100 | Tol. at 15 |

It will be noted that the combination of substituents listed for $R_1$ and $R_2$ in Examples 5 and 6 are not only 100% effective in killing or expelling Haemonchus, but dosages greater than 50 milligrams per kilogram of body weight and less than 100 milligrams per kilogram of body weight are tolerated by the sheep without harmful effects. Other examples also show highly satisfactory results.

In contrast to the good activity of the 2',4'-dichloro congener (Example 5) 100% at 5 mg./kg. and tolerance between 50 and 100 mg./kg., and isomeric compound of the prior art namely the 2', 5'-dichloro (see Monsanto British Pat. No. 1,252,087 published Nov. 3, dichloro substitution as summarized in Table III. It is evident from these data that the shift of one or both of the chlorine atoms from the 2',4' configuration increases toxicity and/or decreases efficacy. This has been mentioned briefly hereinabove. As used herein, "toxic" refers to death of sheep resulting from the use of the indicated compound at the indicated dosage. The 3',5' dichloro compound was not tested for tolerance since its effectiveness was too low to be useful.

Table III

| Example | Position of $R_1$ and $R_2$ Substituents | Effectiveness (%) 5 mg/kg | 15 mg/kg | Tolerance 50 mg/kg | 100 mg/kg |
|---|---|---|---|---|---|
| 23 | 2',4'-dichloro | 100 | 100 | nontoxic | toxic |
| 24 | 2',5'-dichloro | 61 | 100 | toxic | — |
| 25 | 3',4'-dichloro | 20 | 100 | toxic | — |
| 26 | 3',5'-dichloro | — | 67 | — | — |

EXAMPLES 27 THROUGH 30

Similarly, a shift of the substituents for the 2'-methyl-4'-chloro-substituted anilide nolety of Formula I materially reduces efficacy and safety as shown by the following Table IV:

Table IV

| Example | Position of $R_1$ and $R_2$ Substituents | Effectiveness (%) 5 mg/kg | 15 mg/kg | Tolerance 50 mg/kg | 100 mg/kg |
|---|---|---|---|---|---|
| 27 | 2'-methyl-4'-chloro | 95 | 100 | non toxic | toxic |
| 28 | 2'-methyl-3'-chloro | — | 87 | toxic | — |
| 29 | 2'-methyl-5'-chloro | — | 0 | — | — |
| 30 | 2'-methyl-6'-chloro | — | 0 | — | — |

The tolerances of Examples 29 and 30 were not determined, since the compounds were ineffective in combating the parasites in sheep.

EXAMPLES 31 THROUGH 34

For compounds of the present invention (Formula I) having hydrogen in the 2' position of the anilide moiety and chloro, bromo, iodo or trifluoromethyl in the 4' position, the effect of moving the 4'-substituent is shown by the following Table V:

Table V

| Example | Substituent | Effectiveness at 15 mg/kg against Haemonchus 4'-substitution | 3'-substitution | 2'-substitution |
|---|---|---|---|---|
| 31 | Cl | 81 | 0 | 33 |
| 32 | Br | 61 | — | 0 |
| 33 | I | 93 | 00 | 0 |
| 34 | $CF_3$ | 100 | 2 | 0 |

Thus, it is clear that a special and unpredicted superiority is associated with substitution in the 4'-position.

EXAMPLES 35 THROUGH 39

The addition of a third substituent to a 2',4'-dichloro-or 2'-methyl-4'-chloro-substituted anilide moiety is also disadvantageous as shown by the following Table VI:

Table VI

| Example | Effectiveness at 15 mg/kg against Haemonchus | |
|---|---|---|
| 35 | 2',4'-dichloro | 100% |
| 36 | 2',4',5'-trichloro | Toxic |
| 37 | 2',4',6'-trichloro | 73% |
| 38 | 2'-methyl-4'-chloro | 100% |
| 39 | 2',5'-dimethyl-4'-chloro | 0% |

EXAMPLES 40 THROUGH 49

The following Table VII provides physical characteristics including color and melting points of some of the compounds of the present invention. These compounds are solids and were prepared by the process described herein. The compounds are identified by their $R_1$ and $R_2$ substituents in accordance with Formula I.

Table VII

| Example | Substituents $R_1$ | $R_2$ | Color | Melting Point °C |
|---|---|---|---|---|
| 40 | H | Br | Pale Yellow | 136–138 |
| 41 | H | I | Pale Yellow | 143–145 |
| 42 | H | Cl | Off White | 150–152 |
| 43 | H | $CF_3$ | Off White | 175–176 |
| 44 | H | I | Pale Yellow | 143–145 |
| 45 | $CH_3$ | Cl | White | 167–168 |
| 46 | Cl | Cl | Pale Yellow | 150–152 |
| 47 | H | F | Pale Yellow | 205–206 |
| 48 | $CF_3$ | Cl | — | 152.5–153.5 |

Table VII-continued

| Example | Substituents $R_1$ | $R_2$ | Color | Melting Point °C |
|---|---|---|---|---|
| 49 | $CF_3$ | Br | — | 161–163 |

EXAMPLES 50 THROUGH 60

These and the following examples illustrate the dual activity of compounds of the present invention against both Haemonchus and *Fasciola hepatica* as well as the relative inactivity of related compounds which are not of the invention.

The data of the tables were generated using procedures previously described. The compounds tested are disubstituted and, except for Example 50 which is dibromo, are dichloro. Where the position for the substituents is other than 2' and 4', it is indicated. Under the indicated microorganisms, the values given in this and the following tables, should be read as: percentage of microorganism killed/dose in milligrams per kilogram of body weight. Under "Tolerance", the term "Tol." means "tolerated", "Tox." means "toxic", and "Sym." means "symptoms of toxic reaction", all at the dosage value which follows. It will be appreciated that there is no sharp toxicity end point in determining toxicity to living sheep.

Table VIII

| Example | Substituents $R_1$ | $R_2$ | Haemonchus | Fasciola hepatica | Tolerance (mg./kg.) |
|---|---|---|---|---|---|
| 50 | Br | Br | 99.8/5 | 100/5 | — |
| 51 | Cl | Cl | 100/15 | 100/5 | Sym./100 |
| 52 | Cl | Cl | 100/5 | 99/2 | Tol./50 |
| 53 | Cl | Cl | 14/2 | 44/1 | — |
| 54 | Cl | Cl-5' | 100/15 | 100/15 | Tol./50 |
| 55 | Cl | Cl-5' | 61/5 | 0/5 | — |
| 56 | Cl-3' | Cl | 100/15 | 100/15 | Tox./50 |
| 57 | Cl-3' | Cl | 20/5 | 95/5 | Tox./15 |
| 58 | Cl-3' | Cl | — | 0/2 | — |
| 59 | Cl-3' | Cl-5' | 67,49/15 | 100/15 | Tol./40 |
| 60 | Cl-2' | Cl-3' | 14/15 | — | — |

The 2',4' dichloro compound of the invention affords 100% dual activity at a 5 mg./kg. dose against both Haemonchus and Fasciola at a therapeutic ratio of at least 10:1. The 2',5' dichloro compound would not be clinically effective against either parasite at 5 mg./kg., and extrapolation of the results indicate a clinically sufficient dose would be achieved at a therapeutic ratio at a significantly lower level (about 3:1 to 5:1). Against Fasciola, the 2',4' dichloro compound is 99% effective at doses 2.5 times less than that at which the 2',5' dichloro compound was shown to have no activity.

EXAMPLES 61 THROUGH 73

The test data of these examples were obtained as before on compounds having methyl and halo substituents in which halo was chloro, homo, or iodo. The substitutions were at 2',4' unless otherwise noted.

Table IX

| Example | Substituents R₁ | R₂ | Haemonchus | Fasciola hepatica | Tolerance (mg./kg.) |
|---|---|---|---|---|---|
| 61 | CH₃ | Cl | 100/15 | 100/5 | Tox./100 |
| 62 | CH₃ | Cl | 99,95/5 | 0/2 | Sym./50 |
| 63 | CH₃ | Cl | 67/2 | — | Tol./25 |
| 64 | CH₃ | Br | 100/5 | 100/5 | Tox./50 |
| 65 | CH₃ | Br | 38/2 | 100/5 | Sym./50 |
| 66 | CH₃ | I | 88/5 | 100/15 | Sym./50 |
| 67 | CH₃ | I | 13/2 | 100/5 | — |
| 68 | CH₃ | Cl-3' | 87/15 | 0/15 | Tox./50 |
| 69 | CH₃ | Cl-5' | 0/15 | — | — |
| 70 | CH₃ | Cl-6' | 0/15 | — | — |
| 71 | Cl | CH₃ | 62/15 | — | — |
| 72 | Cl-3' | CH₃ | 80/15 | — | — |
| 73 | Cl-3' | CH₃ | 0/5 | — | — |

Table IX demonstrates the much greater dual activity of the methyl 2', chloro 4' compound as well as its greater activity against Haemonchus. In many cases the methyl 2', chloro 4' isomer is very active at doses well below those at which other isomers are inactive.

EXAMPLES 74 THROUGH 81

The data of these examples show in Table X the dual activity of trifluoromethyl 2', and chloro 4' or bromo 4'.

Table X

| Example | Substituents R₁ | R₂ | Haemonchus | Fasciola hepatica | Tolerance (mg./kg.) |
|---|---|---|---|---|---|
| 74 | CF₃ | Cl | 100/15 | 100/2 | Tox./25,50 |
| 75 | CF₃ | Cl | 91/5 | 100/1 | Tol./15 |
| 76 | CF₃ | Cl | 96/2 | — | — |
| 77 | CF₃ | Cl | 76/1 | — | — |
| 78 | CF₃ | Br | 100/5 | 100/5 | Tol./35 |
| 79 | CF₃ | Br | 99.8/2 | 100/2 | Tol./20 |
| 80 | CF₃ | Br | — | 100/1 | — |
| 81 | CF₃ | Br | — | 97/0.5 | — |

The trifluoromethyl 2', chloro or bromo 4' appear to be the most active compounds of the invention, and of these the bromo 4' is preferred.

EXAMPLES 82 THROUGH 96

The data of these examples, shown in Table XI, are based on monsubstitution in the position indicated on the anilide moiety.

Table XI

| Example | Monosubstituent | Haemonchus | Fasciola hepatica |
|---|---|---|---|
| 82 | Cl-4' | 81/15 | 100/15 |
| 83 | Cl-4' | 65/5 | 50/5 |
| 84 | Cl-4' | 0/2 | 0/2 |
| 85 | Cl-3' | 0/15 | — |
| 86 | Cl-2' | 33/15 | — |
| 87 | CF₃-4' | 100/15 | 100/15 |
| 88 | CF₃-3' | 2/15 | — |
| 89 | CF₃-2' | 0/15 | — |
| 90 | Br-4' | 61/15 | 100/15 |
| 91 | Br-4' | — | 0/5 |
| 92 | Br-2' | 0/15 | — |

Table XI-continued

| Example | Monosubstituent | Haemonchus | Fasciola hepatica |
|---|---|---|---|
| 93 | I-4' | 93/15 | 0/15 |
| 94 | I-4' | 22/5 | — |
| 95 | I-3' | 14/15 | — |
| 96 | I-2' | 0/15 | — |

The monsubstituted isomers of 4'-halo, consisting of chloro, bromo, and iodo, and of 4' trifluoromethyl of the present invention have significantly enhanced Haemonchus activity over the 2' and 3' isomers.

While the foregoing describes several embodiments of the present invention, it is understood that the invention may be practiced in still other forms within the scope of the following claims.

I claim:
1. The method for treating a parasite infested or parasite exposed quadruped animal comprising administering orally to said animal an antiparasitically effective but nontoxic quantity of an active ingredient being a 3-tert.-butyl-6-methyl-5-nitrosalicylanilide of the general formula:

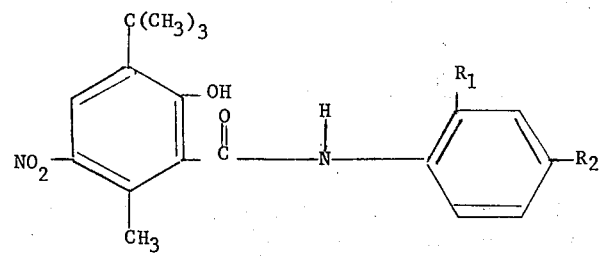

in which
R₁ is H, chloro, bromo, iodo, CF₃ or alkyl of 1 to 4 carbon atoms, and
R₂ is chloro, bromo, iodo or CF₃.
2. The method claim 1 in which the administration is of a curative quantity to a parasite infested animal.
3. The method of claim 1 in which the parasite is a Nematode or a Trematode and the quantity of active ingredient is chosen from about 0.25–50 mg./kg. based on the body weight of the host animal.
4. The method of claim 1 in which the parasite is a Haemonchus or a Fasciola; R₁ is methyl, chloro, bromo, iodo or CF₃ and R₂ is chloro, bromo, iodo or CF₃; and the quantity of active ingredient is chosen from about 0.5–10 mg./kg. based on the body weight of the host animal which is either sheep or cattle.
5. The method of claim 1 in which the parasite is a Fasciola; R₁ is CF₃ and R₂ is bromo; and the quantity of active ingredient is chosen from about 0.5–10 mg./kg. based on the body weight of the host animal which is either sheep or cattle.
6. The method of claim 5 in which the parasite is Fasciola hepatica and the quantity of active ingredient is about 3 mg./kg. based on the body weight of the host animal.
7. The method of claim 5 in which the active ingredient is in the form of a drench, paste, bolus or top dressing.
8. A veterinary composition for antiparasitic use in a host quadruped animal comprising an orally ingestable carrier and admixed therein as an active ingredient an effective but nontoxic quantity of a 3-tert.-butyl-6-methyl-5-nitrosalicylanilide of the formula:

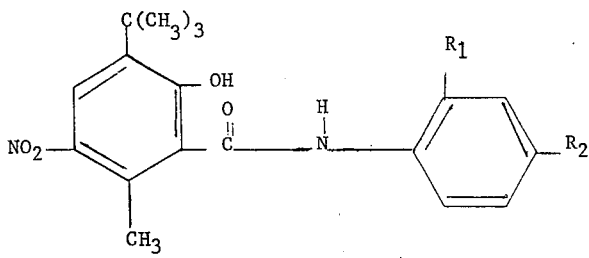

in which
R$_1$ is H, chloro, bromo, iodo, CF$_3$ or alkyl of 1 to 4 carbon atoms, and
R$_2$ is chloro, bromo, iodo or CF$_3$.

9. The veterinary composition of claim 8 in which said carrier contains a curative quantity of said active ingredient for a parasite infected host animal.

10. The composition of claim 8 in which the composition is for use against a Nematode or a Trematode and the effective but nontoxic quantity of active ingredient is chosen from about 0.25–50 mg./kg. based on the body weight of the host animal.

11. The composition of claim 8 in which the parasite is a Haemonchus or a Fasciola; R$_1$ is methyl, chloro, bromo, iodo or CF$_3$ and R$_2$ is chloro, bromo, iodo or CF$_3$; and the quantity of active ingredient is chosen from about 0.5–10 mg./kg. based on the body weight of the host animal which is either sheep or cattle.

12. The composition of claim 8 in which the parasite is a Fasciola; R$_1$ is CF$_3$ and R$_2$ is bromo; and the quantity of active ingredient is chosen from about 0.5–10 mg./kg. based on the body weight of the host animal which is either sheep or cattle.

13. The composition of claim 12 in which the parasite is Fasciola hepatica and the quantity of active ingredient is about 3 mg./kg. based on the body weight of the host animal.

14. The composition of claim 12 in which the active ingredient is in the form of a drench, paste, bolus or top dressing.

* * * * *